United States Patent [19]
Sun

[11] Patent Number: 6,046,373
[45] Date of Patent: Apr. 4, 2000

[54] CATALYTIC CONVERSION OF OXYGENATES TO OLEFINS

[75] Inventor: Hsiang-ning Sun, Houston, Tex.

[73] Assignee: Exxon Chemical Patents Inc., Houston, Tex.

[21] Appl. No.: 09/069,614

[22] Filed: Apr. 29, 1998

[51] Int. Cl.[7] .............................. C07C 1/00; C07F 1/00; B01J 29/04; B01J 27/182
[52] U.S. Cl. .................... 585/640; 585/638; 585/639; 585/906; 204/157.15; 204/157.6; 502/85; 502/214
[58] Field of Search ................................. 585/638, 639, 585/640, 906; 204/157.15, 157.6; 502/85, 214; 423/714

[56] References Cited

U.S. PATENT DOCUMENTS

| | | | |
|---|---|---|---|
| 4,440,871 | 4/1984 | Lok et al. ............................... | 502/214 |
| 4,499,327 | 2/1985 | Kaiser .................................... | 585/640 |
| 4,861,938 | 8/1989 | Lewis et al. ........................... | 585/640 |
| 5,095,163 | 3/1992 | Barger .................................... | 585/640 |
| 5,126,308 | 6/1992 | Barger et al. .......................... | 502/214 |
| 5,191,141 | 3/1993 | Barger et al. .......................... | 585/640 |
| 5,367,100 | 11/1994 | Gongwei et al. ...................... | 585/640 |
| 5,714,662 | 2/1998 | Vora et al. .............................. | 585/640 |
| 5,744,680 | 4/1998 | Mulvaney, III et al. ............... | 585/640 |

FOREIGN PATENT DOCUMENTS

| | | |
|---|---|---|
| WO 93/24431 | 12/1993 | WIPO . |
| WO/97/25272 | 7/1997 | WIPO . |

OTHER PUBLICATIONS

Chang, "Methanol Conversion to Light Olefins," *Catal. Rev.–Sci. Eng.*, 26(3&4), pp. 323–345 (1984).

Kaeding, et al., "Production of Chemicals from Methanol," *Journal of Catalysts*, vol. 64, pp. 155–164 (1980).

*Zeolites*, vol. 17, pp 212–222 (1996).

Atlas of Zeolite Structure Type, Internet Website, pp. 1–2, 1995–96.

*Primary Examiner*—Walter D. Griffin
*Assistant Examiner*—Thuan D. Dang
*Attorney, Agent, or Firm*—Bradley A. Keller

[57] ABSTRACT

A method for preparing a catalyst and the use of such catalyst for converting an oxygenate feed to olefins wherein the catalyst is modified or treated with the aid of electromagnetic energy.

19 Claims, No Drawings

CATALYTIC CONVERSION OF OXYGENATES TO OLEFINS

FIELD OF THE INVENTION

The present invention relates to (i) a method for preparing a catalyst for converting an oxygenate feed to olefins wherein the catalyst is modified or treated with the aid of electromagnetic energy, and (ii) an oxygenate conversion process using the catalyst so prepared.

BACKGROUND OF THE INVENTION

Light olefins (defined herein as ethylene, propylene, butenes and mixtures thereof) serve as feeds for the production of numerous chemicals and polymers. Light olefins traditionally are produced by thermal or catalytic cracking of petroleum or naphtha. Due to the escalating cost/tightening supply of crude petroleum, efforts to develop light olefin production technologies based on alternative feedstocks have increased.

An important type of alternative feedstocks is oxygenates, such as alcohols, particularly methanol, ethers, and carbonates. Alcohols may be produced by fermentation, or from synthesis gas derived from natural gas, petroleum liquids, carbonaceous materials, including coal, recycled plastics, municipal wastes, or any organic material. Because of the wide variety of sources, alcohols, alcohol derivatives, and other oxygenates have promise as an economical, non-petroleum source for olefin production.

Olefins, particularly light olefins, are the most sought after products from oxygenate conversion and petroleum cracking processes. A continuing need exists to improve the catalysts to obtain better catalytic performance and to find faster, more efficient, and/or a more flexible catalyst manufacturing processes.

SUMMARY OF THE INVENTION

The present invention provides a process of converting an oxygenate feed to olefins, said process comprising contacting said oxygenate feed with a catalyst for conversion of oxygenates to olefins under conditions effective to convert said oxygenate feed to a product comprising said olefins wherein said catalyst comprises a solid framework which has been subjected to modification with a modifying agent in the presence of electromagnetic energy comprising a frequency and a power effective to form said catalyst.

DETAILED DESCRIPTION OF THE INVENTION

The present invention provides a method of modifying and treating an oxygenate-to-olefin catalyst comprising a solid framework which has been modified with a modifier in the presence of electromagnetic energy and a catalytic process of using a catalyst so modified/treated in the conversion of an oxygenate feed to olefins. The words "modified" and "treated" (similarly "modification" and "treatment") are used interchangeably and/or conjunctively hereinafter.

The use of electromagnetic energy may reduce reaction time during the catalyst modification processes, and also may make such modification processes more flexible, efficient, and more cost effective. Catalysts with different and/or more desirable catalytic properties that are not otherwise attainable also may be prepared when electromagnetic energy is used. The resulting catalysts may have comparable or better catalytic performance in converting oxygenates to olefins.

Most catalysts that are used in oxygenate conversion and petroleum cracking processes comprise molecular sieve type solid frameworks. Molecular sieves generally comprise a stable solid crystalline framework structure enclosing cavities of molecular dimensions. The cavities form a well-defined microporous system of cages with one-, two- and/or three-dimensional channels. The channels may or may not be connected with one another. The cavities, pores or channels in a given type of molecular sieve have well-defined dimensions which will only allow molecules up to a certain size to enter the pores or channels. The pores can be as small as about 3 Angstroms and as large as about 15 Angstroms or larger. Most catalytic reactions are believed to take place inside of these pores and channels.

The present invention should achieve many of the desired improvements using substantially any molecular sieve catalyst, regardless of the structure type or pore size. Preferred molecular sieve catalysts for use according to the present invention comprise "small" and "medium" pore molecular sieve catalysts. "Small pore" molecular sieve catalysts are defined as catalysts with pores having a diameter of less than about 5.0 Angstroms. "Medium pore" molecular sieve catalysts are defined as catalysts with pores having a diameter in the range of from about 5.0 to about 10.0 Angstroms. "Large pore" molecular sieve catalysts are catalysts with pores having a diameter larger than about 10.0 Angstroms.

A molecular sieve catalyst can be zeolitic (zeolite) or non-zeolitic. Zeolitic molecular sieve catalysts suitable for the use in the present invention with varying degree of effectiveness include, but are not necessarily limited to AEI, AFI, CHA, ERI, FAU, LOV, MON, RHO, THO, MFI, FER, AEL, MEL, and substituted examples of these structural types, as described in W. M. Meier and D. H. Olson, *Atlas of Zeolitic Structural Types* (Butterworth Heineman-third edition, 1997), incorporated herein by reference.

Preferred zeolite catalysts include but are not necessarily limited to zeolite 3A zeolite 4A, zeolite 5A (collectively referred to hereinafter as zeolite A), zeolite X such as zeolite 13X, zeolite Y, zeolite USY, ZK-5, ZSM-5, ZSM-11, ZSM-22, ZSM-34, MCM-41, erionite, chabazite, mordenite, offretite, zeolite L, zeolite beta, borosilicates and mixtures thereof. See Meier and Olson. These zeolites may be obtained from many companies and commercial sources such as Mobil, AMOCO, UCI, Engelhard, Aldrich Chemical Company, Johnson Matthey Company, Union Carbide Corporation, and others.

Zeolites possess acidity as a result of the difference in valences between the two major framework elements—silicon (valence of 4+) and aluminum (valence of 3+). It is believed that many zeolites may have both Lewis acid sites which accept electron donating compounds, functional groups or moieties, and Brønsted acid sites which donate protons ($H^+$ions) to other molecules. Most catalytic reactions take place at or near various acidic sites or in the channels.

In one embodiment of the invention, zeolites are subjected to a "post-synthesis" treatment or modification with a modifying agent in the presence of electromagnetic energy comprising a frequency and a power. The treatment and/or modification is carried out on a zeolite after the zeolite already has been synthesized separately in the same or a different vessel. The modifications may change the composition, the acidity, the nature of acid sites, pore size, pore size distribution, crystallinity, surface area, and other properties of the zeolites. Metal ions such as alkali metal ions, alkaline earth metal ions, transition metal ions, particularly Pd, Pt, and Ir ions, and ions of Cr, Ge, Sn, Ti, Zr, Hf, and others, can be incorporated into either the zeolite framework and/or outside the framework during the modifications. Reactive materials comprising an element selected from the group consisting of B, Al, Si, Mo, W, V, Nb, and mixtures thereof also may be used as modifying agents. Examples of such materials are halides, alkoxides, carboxylates, carbonyls, organometallic derivatives, and mixtures thereof.

Calcination, heat treatment, hydrothermal treatment with steam containing gases, treatment with oxidizing and/or reducing agents, and treatment with organic or inorganic acids such as HF, HCl, HBr, HI, glutaric acid, maleic acid, oxalic acid, and chelating agents such as ethylenediaminetetraacetic acid (EDTA), also can be used to alter the physical, chemical and catalytic properties of zeolites. Steam also may be considered as a modifying agent. In the present invention, all the treatments and/or modifications are carried out in the presence of electromagnetic energy comprising a frequency and a power.

Non-zeolitic molecular sieves also are suitable for use in the present invention. Silicoaluminophosphates (SAPO's), substituted aluminophosphates (substituted ALPO's or MeAPO's), and substituted aluminophosphosilicon oxides (substituted SAPO's or MeAPSO's) have been synthesized and investigated as catalysts for converting oxygenate feeds or cracking heavy hydrocarbons to light olefins. Aluminophosphate molecular sieves (ALPO's) also may be used in the present invention too. These non-zeolitic molecular sieves collectively are referred to herein as "SAPO type" molecular sieves.

SAPO type molecular sieves have a three-dimensional microporous crystalline framework of $PO_2^+$, $AlO_2^-$, $SiO_2$ and/or $MeO_2^m$ tetrahedral units, with or without metals or other substituents in the framework. The "m" superscript represents a net electric charge depending on the valence state of the metal, Me. When Me has valence state of +2, +3, +4, +5, or +6 valence state, "m" is −2, −1, 0, +1, and +2, respectively. "Me" includes, but is not necessarily limited to B, Zn, Mg, Mn, Co, Ni, Ga, Fe, Ti, Zr, Ge, Sn, Cr, and mixtures thereof.

Because an alumninophosphate ($AlPO_4$) framework inherently is neutral in electrical charges, the incorporation of silicon or other metallic or nonmetallic elements into the framework by substitution generates more active catalytic sites, particularly acid sites and increased acidity. Controlling the quantity and location of silicon atoms and other elements incorporated into an $AlPO_4$ framework is important in determining the catalytic properties of a particular SAPO type molecular sieve. Properly adjusted acid strength, acidity distribution, and acid site density are the keys to forming a good oxygenate conversion or petroleum cracking catalyst.

The SAPO type molecular sieve catalysts are modified with a modifier or treated in the presence of electromagnetic energy after they have been synthesized. The "postsynthesis" modification is accomplished by treating a SAPO type molecular sieve—already synthesized separately in the same or a different vessel—in the presence of electromagnetic energy, with metallic, semi-metallic or non-metallic modifiers comprising a compound of an element selected from the group consisting of iron, nickel, cobalt, manganese, lithium, sodium, potassium, rubidium, cesium, beryllium, magnesium, calcium, strontium, barium, palladium, platinum, iridium, copper, silver, gold, boron, indium, gallium, vanadium, niobium, molybdenum, tungsten, zinc, cadmium, titanium, zirconium, hafnium, silicon, germanium, tin, lanthanides, actinides, fluorine, chlorine, bromine, iodine, and mixtures thereof. Steam also may be considered as a modifying agent while such a modification usually is referred to as hydrothermal treatment.

Reactive materials comprising an element selected from the group consisting of B, Al, Si, Mo, W, V, Nb, and mixtures thereof also may be used as modifying agents. Examples of such materials are halides, alkoxides, carboxylates, carbonyls, organometallic derivatives, and mixtures thereof.

A catalyst treatment should be carried out in the presence of electromagnetic energy with and/or without added chemical agents. Typical treatments include, but are not necessarily limited to calcination, hydrothermal treatment with a steam-containing gas, treatment with oxidizing agents (oxidation) or reducing agents (reduction, hydrogenation if hydrogen is the reducing agent), acid treatment, base treatment, chelating agent treatment, and combinations thereof.

Examples of chemical agents suitable for use are inorganic or organic acids, inorganic or organic bases, and chelating agents which include, but are not necessarily limited to hydrogen peroxide, adipic acid, glutaric acid, glutaric anhydride, maleic acid, maleic anhydride, oxalic acid, ethylenediaminetetraacetic acid (EDTA) and its salts, phthalic acid, phthalic anhydride, salicylic acid, ethylene glycol, ethylenediamine, HCl, HBr, HF, HI, $HClO_4$, $HClO_3$, $HBrO_3$, phosphoric acid, phosphorous acid, nitric acid, sulfuric acid, sulfurous acid, formic acid, acetic acid, ammonia, trimethylamine, and mixtures thereof. These chemical agents may or may not become part of the final composition of the treated/modified catalyst.

SAPO type molecular sieves that will convert an oxygenate feed to olefins, and that are suitable for use include, but are not necessarily limited to SAPO-5, SAPO-11, SAPO-17, SAPO-18, SAPO-34, SAPO-44, SAPO-56, CoAPSO-34, NiAPSO-34, CoAPSO-17, NiAPSO-17, MnAPSO-17, CrAPSO's, MgAPSO's, CoAPO's, NiAPO's, MnAPO's, and mixtures thereof. Many of the foregoing SAPO type molecular sieves are available commercially from UOP of Des Plaines, Ill. MeAPO's and MeAPSO's also may be synthesized as described in U.S. Pat. No. 5,126,308. SAPO-17, SAPO-34, and SAPO-44 may be synthesized according to U.S. Pat. No. 4,440,871, incorporated herein by reference, and *Zeolites*, Vol. 17, pp 512–522 (1996), incorporated herein by reference.

SAPO type molecular sieves with small pores—pores smaller than about 5.0 Angstroms—are preferred because they tend to favor light olefin production as a result of sieving effects. A preferred small pore SAPO type molecular sieve is SAPO-34 which has a pore diameter of about 4.3 Angstroms. Other preferred small pore SAPO type molecular sieves include, but are not necessarily limited to SAPO-17, SAPO-18, SAPO-44, CoAPSO-17, NiAPSO-17, MnAPSO-17, CoAPSO-34, NiAPSO-34, CrAPSO-34, and mixtures thereof.

For the chabazite-like or erionite-like SAPO-17, SAPO-18, SAPO-34 and SAPO-44 molecular sieves, it may be possible to incorporate more silicon atoms into the tetrahedral positions of the framework to afford greater flexibility in adjusting acidic properties. Medium pore molecular sieves such as SAPO-11 and large pore molecular sieves such as SAPO-5 may be used to convert oxygenates to olefins, but they tend to produce less light olefins and more heavier hydrocarbons, including aromatics.

Some non-molecular sieve solid framework catalysts also may be useful for the present invention, including, but not necessarily limited to magnesium oxide, gallium oxide, indium oxide, zirconium phosphates, titanium oxide, zirconium oxide, hafnium oxide, silica, niobium oxide, vanadium oxide, heteropoly acids such as 12-silicotungstic acid, 12-silicomolybdic acid, pillared clays, acid treated pillared clays, boron oxide, aluminas, Pd or Pt modified aluminas, fluoride modified aluminas, chloride modified aluminas, fluoride modified Pt or Pd containing aluminas, chloride modified Pt or Pd containing aluminas, Pd or Pt modified silica, crystalline silica-aluminas, amorphous silica-aluminas, and mixtures thereof. These compounds may be obtained from many commercial sources known to a person having ordinary skill in the art, such as W. R. Grace Company, Aldrich Chemical Company, Engelhard, Johnson Matthey, ALCOA, Union Carbide Corporation, Huber, Ethyl Corporation, and others.

Molecular sieves and non-molecular sieves also may be combined, blended, mixed and or admixed chemically, physically, or mechanically to produce catalysts suitable for use in the present invention. Such mixtures may provide better catalytic performance and/or more desirable physical properties—better resistance to attrition, better resistance to poisons, more desirable pore size distributions, surface areas, and particle size distributions.

All catalyst modifications and treatments in the presence of electromagnetic energy for zeolites, non-zeolitic molecular sieves, and non-molecular sieves are carried out under conditions effective to produce a desired catalyst. The reaction temperature is in the range of from about −78° C. to about 800° C. The pressure is not critical. A suitable range for the pressure is from about 1.0 kPa to about 1.0 MPa. The total reaction time of a modification or treatment is in the range of from about 0.01 second to about 24 hours.

Preferably, calcination, heat treatment, and hydrothermal treatment are carried out in the temperature range of from about 120° C. to about 750° C. For hydrothermal treatment, the steam partial pressure is in the range of from about 1.0 kPa to about 500 kPa. The steam may be mixed with another gas or gas mixture. Air or oxygen containing gas are preferred for oxidation treatment. Gases comprising hydrogen, CO, and mixtures thereof are preferred for reduction/hydrogenation treatments.

A solvent may be used for catalyst modification and/or treatment. It is preferable to use a solvent for ion exchange or ion incorporation modifications. Any solvent is suitable provided that the solvent does not substantially interfere with the intended interaction between the catalyst and the electromagnetic energy selected. Solvents also can be used for washing the modified catalyst after the initial modification. Preferred solvents include, but are not necessarily limited to water, alcohols such as methanol, ethanol, alkanes such as n-pentane, n-hexane, or n-heptane, aromatic compounds such as benzene, toluene, o-xylene, m-xylene, p-xylene, and mixtures thereof These solvents are removed later by methods such as filtration, centrifugation, drying, distillation, or a combination thereof.

The modifications and treatments may be carried out in substantially any atmosphere. Preferred atmospheres include, but are not necessarily limited to air, nitrogen, hydrogen, argon, helium, neon, krypton, oxygen, steam, carbon dioxide, carbon monoxide, methane, ethane, propane, and mixtures thereof.

If desirable, the catalyst may be further treated after modification by other methods or processes, which include, but are not necessarily limited to washing, sedimentation, centrifugation, drying, spray drying, calcination, sizing, pelletizing, forning, blending, grinding, milling, addition of binders and/or fillers, or combinations thereof.

The process of catalyst modification and/or treatment may be batch, stepwise, continuous, semi-continuous, or combinations thereof. Conventional chambers may be used, or a chamber that is specifically designed to focus the electromagnetic energy on the catalyst may be used. In addition, inert packing materials and/or electromagnetic energy reflecting compounds may be mixed with the catalyst to increase the efficiency of the interaction between the electromagnetic energy and the catalyst.

In the oxygenate conversion process, the oxygenate feed is converted to the olefins at a desired rate under conditions effective to reach a desired selectivity to olefins. In a preferred embodiment, the conversion of the oxygenate feed is at least about 70% and the combined selectivity to all olefins is at least about 50 wt % of the converted oxygenate on a water or $H_rX$ free basis where X is a heteroatom other than oxygen existing in the "oxygenate feed" such as halogens, nitrogen or sulfur. The subscript "r" represents the valence state of X. For example, "r" is 1 for halogens, 2 for sulfur, and 3 for nitrogen. The catalytic performance of a catalyst which has been treated or modified in the presence of electromagnetic energy may be equal to or better than that which has been treated or modified without exposure to electromagnetic energy.

The electromagnetic energy useful for catalyst modifications in the present invention comprises a frequency in the microwave region—a frequency in the range of from about 10 MHz to about 50,000 MHz, preferably in the range of from about 100 MHz to about 35,000 MHz, more preferably from about 2000 MHz to about 30,000 MHz. The electromagnetic energy should have a power in the range of from about 0.01 watt to about 100,000 watts, preferably in the range of from about 0.1 watt to about 1,000 watts, more preferably from about 1.0 watt to about 100 watts. Treatment of larger amounts of catalyst would require more power.

Electromagnetic energy having more than one frequency with the same or different powers may be used simultaneously or not simultaneously. If the electromagnetic energy having the same or different frequencies is not applied simultaneously during the catalyst modification/treatment process, then preferably the energy is applied in series, in pulses, consecutively, or in combinations thereof. In addition, from about one frequency to about nine different frequencies may be used. Preferably, a total of from about one frequency (no additional frequency) to about five frequencies (four additional frequencies) may be used.

Electromagnetic energy comprising different frequencies or electromagnetic energy having the same frequency from separate sources may be applied to different components of the catalyst or the modifying agents simultaneously, not simultaneously, consecutively, or, in combinations thereof. The electromagnetic energy may be applied in various modes—continuous, semi-continuous, intermittent, pulsing, or combinations thereof.

The time periods for applying the electromagnetic energy will depend on the frequency and power of the electromagnetic energy applied, the mode of application, the catalyst to be treated, chemical agents and/or modifiers used, temperature, pressure, and other modification/treatment conditions. For each individual application of or exposure to electromagnetic energy, the time period generally is in the range of from about 0.001 seconds to about 240 minutes, preferably from about 0.05 seconds to about 120 minutes, most preferably from about 0.5 second to about 100 minutes.

The process for converting oxygenate feeds to olefins employs an organic starting material (feedstock) preferably comprising "oxygenates." As used herein, the term "oxygenates" or "oxygenate feed" is defined to include, but not necessarily limited to aliphatic alcohols, ethers, carbonyl compounds (aldehydes, carboxylic acids, carbonates, and the like), and also compounds containing hetero-atoms, such as, halides, mercaptans, sulfides, amines, and mixtures thereof. The aliphatic moiety of an oxygenate feed preferably should contain in the range of from about 1 to about 10 carbon atoms and more preferably in the range of from about 1 to about 4 carbon atoms.

Representative oxygenates include, but are not necessarily limited to, lower straight chain or branched aliphatic alcohols, their unsaturated counterparts, their esters, and their nitrogen, halogen and sulfur analogues. Examples of suitable compounds include, but are not necessarily limited to: methanol; ethanol; n-propanol; 2-propanol; n-butanol, sec-butanol, t-butanol, isobutanol, $C_5$–$C_{10}$ alcohols; $C_2$–$C_{10}$ aliphatic diols; methyl ethyl ether; dimethyl ether; diethyl ether; di-isopropyl ether; dimethyl sulfide; diethyl sulfide; methyl mercaptan, ethyl mercaptan; methylamine; dimethylamine, trimethylamine, ethylamine; diethylamine, triethylamine, methyl bromide, ethyl bromide, methyl chloride, ethyl chloride; methyl iodide, ethyl iodide, formaldehyde; di-methyl carbonate; di-methyl ketone; n-alkyl amines, n-alkyl halides, and n-alkyl sulfides having n-alkyl groups of comprising the range of from about 3 to about 10 carbon atoms; and mixtures thereof. As used herein, the term "oxygenate", "oxygenate feed" or "oxygenate feedstock" designates only the organic material used as the feed. The total charge of a feed to the reaction zone may contain additional compounds such as diluents.

A more preferred oxygenate comprises a compound selected from the group consisting of methanol, ethanol, dimethyl ether, methyl ethyl ether, diethyl ether, dimethyl carbonate, methyl formate, and mixtures thereof.

Preferably, the oxygenate feed should be contacted in the vapor phase in a reaction zone with the selected molecular sieve catalyst at effective process conditions so as to produce the desired olefins, i.e., an effective temperature, pressure, WHSV (weight hourly space velocity) and, optionally, an effective amount of diluent.

Alternately, the process may be carried out in a liquid, supercritical fluid, a mixed vapor/liquid, or a mixed vapor/supercritical fluid phase. When the process is carried out in such phases, different conversions and selectivities of feedstock-to-product may result depending upon the catalyst and reaction conditions.

The temperature employed in the oxygenate conversion process may vary over a wide range depending, at least in part, on the composition of the oxygenate feed, the desired products, the selected catalyst and the reactor configuration. Although not limited to a particular temperature, best results will be obtained if the process is conducted at temperatures in the range of from about 200° C. to about 700° C., preferably in the range of from about 250° C. to about 650° C., and most preferably in the range of from about 300° C. to about 600° C. Lower temperatures generally result in lower rates of reaction, and the formation of the desired light olefin products may become markedly slow. However, at higher temperatures, the process may not form an optimum amount of light olefin products, and the coking rate may become too high.

Olefin products, particularly light olefins, will form— although not necessarily in optimum amounts—at a wide range of pressures, including but not limited to autogeneous pressures and pressures needed to maintain a super critical state. The pressures generally are in the range of from about 10 Pa to about 500 MPa. A preferred pressure is in the range of from about 1.0 kPa to about 17 MPa, most preferably in the range of from about 50 kPa to about 5 MPa. The foregoing pressures are exclusive of diluent, if any is present, and refer to the partial pressure of the feedstock as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins such as ethylene still may form.

When the oxygenate feed comprises mainly alcohols, ethers may become the major products under conditions not effective or sufficient to produce olefins.

The process should be continued for a period of time sufficient to produce the desired olefin products under the given reaction conditions. The reaction time may vary from tenths of a second to a few hours. The reaction time is largely determined by the reactor type, reaction temperature, the pressure, the catalyst selected, the weight hourly space velocity, the reaction phase (liquid, vapor, supercritical fluid, or mixed), and the selected process design characteristics.

The feedstock may have a wide range of weight hourly space velocities (WHSV), defined as weight feed per hour per weight of catalyst. The WHSV generally should be in the range of from about 0.01 $hr^{-1}$ to about 10,000 $hr^{-1}$, preferably in the range of from about 0.05 $hr^{-1}$ to about 5000 $hr^{-1}$, and most preferably in the range of from about 0.1 $hr^{-1}$ to about 2500 $hr^{-1}$. Because the catalyst may contain other materials which act as inerts, fillers, or binders the WHSV herein is calculated on the weight basis of oxygenate feed and catalyst.

One or more diluents may be fed to the reaction zone with the oxygenate feed, such that the total feed mixture comprises diluent in a range of from about 1 mol % to about 99 mol %. Diluents which may be employed in the process include, but are not necessarily limited to helium, neon, argon, krypton, nitrogen, carbon monoxide, carbon dioxide, water (as steam under some reaction conditions), hydrogen, long-chain paraffins, other hydrocarbons (such as methane and ethane, etc.), aromatic compounds, and mixtures thereof. It is preferred that the diluents are substantially inert, stable or incapable of interfering with production of the desired products under the oxygenate conversion conditions. Preferred diluents are water, nitrogen, and mixtures thereof.

A variety of reactor systems may be used to practice the present invention. Such reactor systems include but are not necessarily limited to a fluidized bed reactor, a circulating fluid bed reactor with continuous regeneration, a riser reactor, a fixed bed reactor and a moving bed reactor.

The invention will be better understood with reference to the following examples which are intended to illustrate, but not to limit the present invention.

EXAMPLE I

A strontium containing solution is prepared by dissolving 0.21 grams of strontium acetate (Aldrich Chemical Company) in 18 ml of de-ionized water at room temperature. This solution is mixed with 3.0 grams of SAPO-34 powder obtained from UOP at room temperature. This mixture is placed in a microwave chamber and treated with electromagnetic energy having a frequency of 2450 MHz and a power of 10 watts for three minutes. The solid product is filtered, and then washed with 20 ml of de-ionized water twice. The recovered product then is dried at 110° C. for two hours in air, followed by calcination at 550° C. for sixteen hours in air. Elemental analysis shows that the resulting catalyst has a metal loading of 2.4 wt % strontium.

EXAMPLE II

Example I is repeated except that the SAPO-34 powder is replaced with a SAPO-17 powder which is obtained from UOP. Elemental analysis shows that the resulting catalyst has a metal loading of 1.9 wt % strontium.

EXAMPLE III

A calcium containing solution is prepared by dissolving 0.18 grams of calcium acetate (Aldrich Chemical Company) in 20 ml of de-ionized water at room temperature. This solution is mixed with 3.0 grams of SAPO-34 powder obtained from UOP at room temperature. This mixture is placed in a chamber and treated with electromagnetic energy having a frequency of 2450 MHz and a power of 10 watts for three minutes. The solid product is filtered, and then washed with 20 ml of de-ionized water twice. The recovered product then is dried at 110° C. in air for two hours, followed by calcination at 550° C. in air for sixteen hours. 2.85 g of the catalyst product is obtained. The resulting catalyst has a metal loading of 1.1 wt % calcium.

EXAMPLE IV

An experiment similar to EXAMPLE I is carried out except that 3.0 grams of ZSM-34 molecular sieve are used as the catalyst to replace the SAPO-34 catalyst. The resulting catalyst has a metal loading of 2.1 wt % strontium.

EXAMPLE V

An experiment similar to EXAMPLE I is carried out except that 5.0 grams of ZSM-5 with a silicon-to-aluminum atomic ratio of 280 are used as the catalyst to replace the SAPO-34 catalyst. The resulting catalyst has a strontium loading of 1.22 wt %.

EXAMPLE VI

A barium containing solution is prepared by dissolving 0.27 grams of barium acetate (Aldrich Chemical Company) in 35 ml of de-ionized water at room temperature. This solution is added to 3.2 grams of SAPO-34 powder. The mixture is treated in a microwave chamber with electromagnetic energy of 2,450 MHz and a power of 10 watts for two minutes. The solid product is filtered, and then washed twice with 20 ml of de-ionized water each. The recovered product is dried at 110° C. for three hours, followed by calcination at 550° C. for eight hours in air. The resulting catalyst has a barium loading of 1.98 wt %.

EXAMPLE VII 7.5 grams of SAPO-34 powder are placed in a quartz tube. The SAPO is treated with a stream containing 85 mole % steam and 15 mole % nitrogen at 30 ml/min at 250° C. for 2 hours in the presence of an electromagnetic energy comprising a frequency of 2450 MHz and a power of 40 watts. The catalyst is then allowed to cool to room temperature in a stream containing only nitrogen at 120° C. for 30 minutes. 7.1 grams of hydrothermally treated catalyst are obtained.

EXAMPLE VIII 5.0 grams of SAPO-34 powder and 10 ml of n-hexane which has been dried over sodium are placed in a Teflon® chamber. A solution prepared from mixing 0.3 grams of silicon tetra-ethoxide, $Si(OCH_2CH_3)_4$, with 10 ml of n-hexane which has been dried over sodium is added dropwise to the SAPO-34/n-hexane mixture with vigorous agitation and simultaneous exposure to an electromagnetic energy having a frequency of 2,450 MHz and a power of 5 watts. The mixture is filtered, dried at 110° C. in air for 30 minutes, followed by calcination at 550° C. for 4 hours. 4.9 grams of silicon-treated SAPO-34 are recovered.

EXAMPLE IX

The catalysts prepared according to EXAMPLES I–VI are evaluated as follows:

Samples of 5 cc (approximately 2.7 grams) each of the catalysts are mixed with 15 cc of 3 mm quartz beads and loaded into ¾" outer diameter 316 stainless steel tubular reactors which are heated by a three zone electric furnace. The first zone, acting as the preheating zone, vaporizes the feed at 400° C. The temperature of the center zone of the furnaces is adjusted to 450° C. and the exit pressure is maintained at about 1.5 psig (112 kPa). The bottom zone temperature is set high enough, usually at about 350° C., to ensure that the effluent from the reactor remains in the vapor state. The effluent is sent to the gas chromatographs for analyses.

The reactors are first purged with nitrogen at 50 cc/min flow rate for 30 minutes. The feed to each reactor is a 4:1 ratio mixture of distilled water to methanol, respectively. The feed is pumped into the reactors with an ISCO® pump and calibrated to give a flow rate of about 0.8 $h^{-1}$ WHSV. The effluents are analyzed at pre-determined intervals by on-line gas chromatographs fits with both thermal conductivity detectors and flame ionization detectors.

The Table below shows analyses of the effluents— methanol conversions and the combined selectivities to $C_2$–$C_4$ olefins in weight percent (excluding water).

TABLE

| Catalyst | Methanol Conversion (%) | Total $C_2^=$–$C_4^=$ Selectivity (wt %) |
| --- | --- | --- |
| EXAMPLE I | 100 | 91 |
| EXAMPLE II | 97 | 81 |
| EXAMPLE III | 99 | 84 |
| EXAMPLE IV | 90 | 73 |
| EXAMPLE V | 82 | 61 |
| EXAMPLE VI | 99 | 79 |
| EXAMPLE VII | 100 | 93 |
| EXAMPLE VIII | 98 | 88 |

The foregoing examples demonstrate that high oxygenate feed conversions and high selectivities to olefins can be achieved using catalysts which have been modified and/or treated in the presence of electromagnetic energy. The time and temperature required to modify and/or treat catalysts can be reduced in the presence of electromagnetic energy without adverse effects on the catalyst performance.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

I claim:

1. A process for converting an oxygenate feed to an olefin product, said process comprising contacting said oxygenate feed with a catalyst containing a modified molecular sieve under conditions effective to convert said oxygenate feed to an olefin product, wherein said modified molecular sieve has been modified by contacting a molecular sieve with a modifying agent and applying electromagnetic energy at a frequency and a power effective to modify said molecular sieve.

2. The process of claim 1 wherein said molecular sieve is a zeolite.

3. The process of claim 1 wherein said molecular sieve is a non-zeolitic molecular sieve.

4. The process of claim 2 wherein said zeolite is selected from the group consisting of ZSM-5, ZSM-11, ZSM-22, ZSM-34, silicalite, mordenite, offretite, chabazite, erionite. zeolite A, zeolite X, zeolite Y, zeolite USY, ZK-5, zeolite L, zeolite beta, MCM-41, borosilicates and mixtures thereof.

5. The process of claim 3 wherein said non-zeolitic molecular sieve is selected from the group consisting of a silicoaluminophosphate (SAPO), a substituted SAPO (MeAPSO), an aluminophosphate (ALPO), a substituted ALPO (MeAPO), and mixtures thereof.

6. The process of claim 5 wherein said SAPO is selected from the group consisting of SAPO-5, SAPO-11, SAPO-17, SAPO-18, SAPO-34, SAPO-44, SAPO-56, and mixtures thereof.

7. The process of claim 3 wherein said non-zeolitic molecular sieve is selected from the group consisting of SAPO-17, SAPO-18, SAPO-34, SAPO-44, CoAPSO-17, CoAPSO-34, NiAPSO-17, NiAPSO-34, MnAPSO-17, and mixtures thereof.

8. The process of claim 2 wherein said molecular sieve is selected from the group consisting of ZSM-5, ZSM-34, ZK-5, offretite, chabazite, erionite, and mixtures thereof.

9. The process of claim 1 wherein said frequency is in the range of from about 10 MHz to about 50,000 MHz and said power is in the range of from about 0.01 watt to about 100,000 watts.

10. The process of claim 1 wherein said frequency is in the range of from about 100 MHz to about 35,000 MHz and said power is in the range of from about 1 watt to about 1000 watts.

11. The process of claim 1 wherein said frequency further comprises from about one to about nine additional frequencies.

12. The process of claim 11 wherein said additional frequencies are applied simultaneously.

13. The process of claim 1 wherein said olefin product comprises light olefins.

14. A process for converting an oxygenate feed to an olefin product comprising contacting an oxygenate feed with a catalyst under conditions effective to convert said oxygenate feed to an olefin product, wherein said catalyst comprises a modified SAPO molecular sieve wherein said modified SAPO molecular sieve has been modified by contacting a SAPO molecular sieve with a modifying agent in a reaction system and applying electromagnetic energy to the reaction system at a frequency and a power effective to modify said SAPO molecular sieve.

15. The process of claim 14 wherein said SAPO molecular sieve is selected from the group consisting of SAPO-17, SAPO-18, SAPO-34, SAPO-44, and mixtures thereof.

16. The process of claim 14 wherein said frequency is in the range of from about 10 MHz to about 50,000 MHz and said power is in the range of from about 0.1 watt to about 5000 watts.

17. The process of claim 14 wherein said frequency further comprises from about one to about nine additional frequencies in the range of 10 MHz to about 50,000 MHz.

18. A process for converting an oxygenate feed to an olefin product comprising contacting an oxygenate feed comprising methanol with a catalyst comprising a modified SAPO-34 molecular sieve under conditions effective to produce an olefin product comprising light olefins, wherein said modified SAPO-34 molecular sieve has been modified by treating a SAPO-34 with a modifier comprising an alkaline earth metal ion selected from the group consisting of magnesium ion, calcium ion, strontium ion, barium ion, and mixtures thereof and applying electromagnetic energy at a frequency in the range of from about 10 MHz to about 50,000 MHz and a power in the range of from about 0.01 watt to about 100,000 watts to modify said SAPO-34 molecular sieve.

19. A method for converting an oxygenate to a product comprising olefins, said method comprising contacting an oxygenate with a modified non-zeolitic molecular sieve under conditions effective to convert the oxygenate to a product; said modified non-zeolitic molecular sieve having been modified by contacting a non-zeolitic molecular sieve with a modifying agent and applying electromagnetic energy to modify said non-zeolitic molecular sieve, wherein said oxygenate comprises a compound selected from the group consisting of methanol, dimethyl ether, methylethyl, ether, ethanol, ethyl formate, dimethyl carbonate, and mixtures thereof, said olefins comprise light olefins; said non-zeolitic molecular sieve is selected from the group consisting of SAPO-17, SAPO-18, SAPO-34, SAPO-44, and mixtures thereof; and said electromagnetic energy is applied at a frequency and a power effective to modify said non-zeolitic molecular sieve.

* * * * *